US011291702B1

(12) United States Patent
Shade et al.

(10) Patent No.: US 11,291,702 B1
(45) Date of Patent: Apr. 5, 2022

(54) LIVER ACTIVATION NANOEMULSION, SOLID BINDING COMPOSITION, AND TOXIN EXCRETION ENHANCEMENT METHOD

(71) Applicant: Quicksilver Scientific, Inc., Lafayette, CO (US)

(72) Inventors: Christopher W. Shade, Lafayette, CO (US); Steven Tieu, Lafayette, CO (US)

(73) Assignee: Quicksilver Scientific, Inc., Louisville, CO (US)

( * ) Notice: Subject to any disclaimer, the term of this patent is extended or adjusted under 35 U.S.C. 154(b) by 0 days.

(21) Appl. No.: 16/849,654

(22) Filed: Apr. 15, 2020

Related U.S. Application Data

(60) Provisional application No. 62/834,013, filed on Apr. 15, 2019.

(51) Int. Cl.
| | |
|---|---|
| A61K 36/288 | (2006.01) |
| A61K 31/381 | (2006.01) |
| A61K 31/404 | (2006.01) |
| A61K 31/355 | (2006.01) |
| A61K 36/328 | (2006.01) |
| A61K 47/14 | (2017.01) |
| A61K 47/44 | (2017.01) |
| A61K 9/00 | (2006.01) |
| A61K 9/107 | (2006.01) |
| A61K 36/515 | (2006.01) |
| B82Y 5/00 | (2011.01) |

(52) U.S. Cl.
CPC .......... *A61K 36/288* (2013.01); *A61K 9/0053* (2013.01); *A61K 9/1075* (2013.01); *A61K 31/355* (2013.01); *A61K 31/381* (2013.01); *A61K 31/404* (2013.01); *A61K 36/328* (2013.01); *A61K 36/515* (2013.01); *A61K 47/14* (2013.01); *A61K 47/44* (2013.01); *B82Y 5/00* (2013.01)

(58) Field of Classification Search
CPC .... A61K 36/288; A61K 31/381; A61K 47/14; A61K 31/404; A61K 9/1075; A61K 36/328; A61K 9/0053; A61K 47/44; A61K 36/515; A61K 31/355; B82Y 5/00
See application file for complete search history.

(56) References Cited

U.S. PATENT DOCUMENTS

| | | | |
|---|---|---|---|
| 5,238,683 A | 8/1993 | Crystal | |
| 5,260,065 A | 11/1993 | Mathur et al. | |
| 5,395,619 A | 3/1995 | Zalipsky et al. | |
| 5,565,439 A | 10/1996 | Piazza et al. | |
| 5,569,464 A | 10/1996 | Endo et al. | |
| 5,711,965 A | 1/1998 | Ghyczy et al. | |
| 5,817,695 A | 10/1998 | Pellico | |
| 5,834,014 A | 11/1998 | Weiner et al. | |
| 5,871,769 A | 2/1999 | Fleming et al. |
| 5,935,588 A | 8/1999 | Afriat et al. |
| 6,048,886 A | 4/2000 | Neigut |
| 6,143,786 A | 11/2000 | Gohman et al. |
| 6,159,500 A | 12/2000 | Demopoulos et al. |
| 6,180,662 B1 | 1/2001 | Lanzendorfer et al. |
| 6,204,248 B1 | 3/2001 | Demopoulos et al. |
| 6,218,436 B1 | 4/2001 | Howard et al. |
| 6,235,271 B1 | 5/2001 | Luther et al. |
| 6,245,797 B1 | 6/2001 | Winokur |
| 6,287,611 B1 | 9/2001 | Morello et al. |
| 6,319,517 B1 | 11/2001 | Cavallo et al. |
| 6,337,065 B1 | 1/2002 | Jacobson et al. |
| 6,358,516 B1 | 3/2002 | Harod |
| 6,492,410 B1 | 12/2002 | Leopold et al. |
| 6,534,540 B2 | 3/2003 | Kindness et al. |
| 6,562,369 B2 | 5/2003 | Luo et al. |
| 6,596,305 B1 | 7/2003 | Edgerly-Plug |
| 6,630,157 B1 | 10/2003 | Horrobin et al. |
| 6,713,533 B1 | 3/2004 | Panzner |
| 6,764,693 B1 | 7/2004 | Smith |
| 7,825,084 B2 | 11/2010 | Harris et al. |
| 8,067,381 B1 | 11/2011 | Harris et al. |
| 8,114,913 B1 | 2/2012 | Guilford et al. |
| 8,147,869 B2 | 4/2012 | Guilford et al. |
| 8,252,325 B2 | 8/2012 | Guilford et al. |

(Continued)

FOREIGN PATENT DOCUMENTS

| | | |
|---|---|---|
| EP | 0834301 | 4/1998 |
| WO | WO 9111117 | 8/1991 |

(Continued)

OTHER PUBLICATIONS

Hsu et al. (Use of Lipid Nanocarriers to Improve Oral Delivery of Vitamins, Nutrients 2019, 11, 68). (Year: 2019).*
Farina et al, Metals, Oxidative Stress and Neurodegeneration: A focus on Iron, Manganese and Mercury, Neurochem Int., Apr. 2013, 62(5): 575-594.
Kale et al, Emulsion Micro Emulsion and Nano Emulsion: A Review, Systematic Reviews in Pharmacy, Sys Rev Pharm. 2017; 8(1): 39-47.
Arno Hazekamp, The Trouble with CBD Oil, S. Karger AG, Basel, Med Cannabis Cannabinoids 2018;1:65-72.
Tan et al, Tocotrienols Vitamin E Beyond Tocopherols, CRC Press, Tocotrienols Second Edition, Sec. 2.3, 11-16-16.

(Continued)

*Primary Examiner* — Snigdha Maewall
(74) *Attorney, Agent, or Firm* — Blanchard & Associates

(57) ABSTRACT

An intra-oral, nanoemulsion blend is provided that enhances liver and toxin excretion performance in mammals when orally administered. A solid powder toxin binding composition also is provided that may be used to irreversibly bind the toxins reaching the bowel so that once the toxins are excreted into the bowel, they may not be reabsorbed, and are thus eliminated. A method of administering the nanoemulsion blend and the toxin binding composition to enhance toxin excretion also is described. The nanoemulsion blend is ingestible and edible.

23 Claims, 5 Drawing Sheets

(56) References Cited

U.S. PATENT DOCUMENTS

| | | | |
|---|---|---|---|
| 8,282,977 B2 * | 10/2012 | Bromley | A61K 31/122 426/602 |
| 8,349,359 B2 | 1/2013 | Guilford et al. | |
| 8,679,530 B2 | 3/2014 | Guilford et al. | |
| 8,741,373 B2 | 6/2014 | Bromley et al. | |
| 9,474,725 B1 | 10/2016 | Reillo et al. | |
| 9,730,911 B2 | 8/2017 | Verzura et al. | |
| 9,839,612 B2 | 12/2017 | Reillo et al. | |
| 9,925,149 B2 | 3/2018 | Kaufman | |
| 9,972,680 B2 | 5/2018 | Reillo et al. | |
| 9,974,739 B2 | 5/2018 | Reillo et al. | |
| 10,016,389 B2 | 7/2018 | Zhang | |
| 10,084,044 B2 | 9/2018 | Reillo et al. | |
| 10,103,225 B2 | 10/2018 | Reillo et al. | |
| 10,239,808 B1 | 3/2019 | Black et al. | |
| 2002/0025313 A1 | 2/2002 | Micklus et al. | |
| 2002/0048551 A1 | 4/2002 | Keller et al. | |
| 2002/0102316 A1 | 8/2002 | Weissman | |
| 2002/0106339 A1 | 8/2002 | Fisher et al. | |
| 2002/0132781 A1 | 9/2002 | Kindness et al. | |
| 2002/0137785 A1 | 9/2002 | Kindness et al. | |
| 2002/0169195 A1 | 11/2002 | Kindness et al. | |
| 2002/0182585 A1 | 12/2002 | Kindness et al. | |
| 2002/0187130 A1 | 12/2002 | Kindness et al. | |
| 2003/0059462 A1 | 3/2003 | Barenholz et al. | |
| 2003/0083241 A1 | 5/2003 | Young | |
| 2003/0096000 A1 | 5/2003 | Solis et al. | |
| 2003/0162829 A1 | 8/2003 | Kindness et al. | |
| 2003/0157220 A1 | 9/2003 | Morello et al. | |
| 2004/0022841 A1 | 2/2004 | Hassan et al. | |
| 2004/0022873 A1 | 2/2004 | Guilford et al. | |
| 2004/0127476 A1 | 7/2004 | Kershman et al. | |
| 2004/0170560 A1 | 9/2004 | Fossheim et al. | |
| 2004/0219123 A1 | 11/2004 | Astruc et al. | |
| 2005/0131041 A1 | 6/2005 | Salman et al. | |
| 2005/0191343 A1 | 9/2005 | Liang | |
| 2006/0099244 A1 | 5/2006 | Guilford et al. | |
| 2006/0106093 A1 | 5/2006 | Rich et al. | |
| 2007/0065456 A1 | 3/2007 | Woods | |
| 2008/0131496 A1 | 6/2008 | Guilford et al. | |
| 2008/0207679 A1 | 8/2008 | Berkowitz | |
| 2009/0047340 A1 | 2/2009 | Guilford et al. | |
| 2009/0068253 A1 | 3/2009 | Guilford et al. | |
| 2009/0069279 A1 | 3/2009 | Astruc et al. | |
| 2010/0086573 A1 | 4/2010 | Anderson | |
| 2010/0166846 A1 | 6/2010 | Guilford et al. | |
| 2010/0173882 A1 | 7/2010 | Giliyar et al. | |
| 2010/0233193 A1 | 9/2010 | Guilford et al. | |
| 2010/0233297 A1 | 9/2010 | Guilford et al. | |
| 2010/0291196 A1 | 11/2010 | Guilford et al. | |
| 2010/0316700 A1 | 12/2010 | Guilford et al. | |
| 2011/0020436 A1 | 1/2011 | Guilford et al. | |
| 2011/0129523 A1 | 6/2011 | Guilford et al. | |
| 2011/0274625 A1 | 11/2011 | Redelmeier et al. | |
| 2011/0305752 A1 | 12/2011 | Guilford et al. | |
| 2012/0087994 A1 | 4/2012 | Guilford et al. | |
| 2012/0135068 A1 | 5/2012 | Guilford et al. | |
| 2012/0141608 A1 | 6/2012 | Guilford et al. | |
| 2012/0171280 A1 | 7/2012 | Zhang | |
| 2012/0219616 A1 | 8/2012 | Guilford et al. | |
| 2012/0282325 A1 | 11/2012 | Tong et al. | |
| 2013/0045271 A1 | 2/2013 | Dadey et al. | |
| 2013/0231297 A1 | 9/2013 | Krawitz | |
| 2014/0161784 A1 | 6/2014 | Westerlund et al. | |
| 2015/0079156 A1 | 3/2015 | Kett et al. | |
| 2015/0296856 A1 | 10/2015 | Chandra et al. | |
| 2016/0000710 A1 * | 1/2016 | Gupta | A61K 31/7042 424/450 |
| 2016/0023826 A1 * | 1/2016 | Edwards | A23L 2/02 426/99 |
| 2016/0166516 A1 | 6/2016 | Gannon et al. | |
| 2016/0263047 A1 | 9/2016 | Kaufman et al. | |
| 2017/1277712 | 5/2017 | Yiannios | |
| 2018/0263283 A1 | 9/2018 | Popplewell et al. | |
| 2020/0170272 A1 * | 6/2020 | Bromley | A23L 25/10 |

FOREIGN PATENT DOCUMENTS

| | | |
|---|---|---|
| WO | WO 98/55075 | 12/1998 |
| WO | WO 01/26618 | 4/2001 |
| WO | WO 2008/100629 | 8/2008 |
| WO | WO 2012/066334 | 5/2012 |
| WO | WO 2016/020485 | 2/2016 |

OTHER PUBLICATIONS

Amory et al, Oral Testosterone in Oil Plus Dutasteride in Men: A Pharmacokinetic Study, The Endocrine Society, J. Clin of Endocrinol Metab, May 2005, 90(5):2610-2617.

Peter Casson, MD, Delivery of dehydroepiandrosterone to premenopausal women: Effects of micronization & nonoral administration, Feb. 1996, 649-653.

Dilova et al., Increasing the Solubility of a Poor Soluble API-milk Thistle dry extract (Silymarin), Pharmacia, vol. 61, No. 1/2014.

\* cited by examiner

LIVER ACTIVATION NANOEMULSION, SOLID BINDING COMPOSITION, AND TOXIN EXCRETION ENHANCEMENT METHOD

REFERENCE TO RELATED APPLICATIONS

This application claims the benefit of U.S. Provisional Application No. 62/834,013 entitled "Liver Activation Nanoemulsion, Solid Binding Composition, and Toxin Excretion Enhancement Method" filed Apr. 15, 2019, which is incorporated by reference in its entirety.

BACKGROUND

An adult human liver weighs approximately three pounds. Among many functions, the liver stores minerals, such as iron, and vitamins; regulates blood clotting; metabolizes fats, carbohydrates and protein into the molecules that provide energy for cell metabolism; synthesizes proteins the body uses to repair and grow cells; and regulates use of fat stores. The liver also plays a role in maintaining proper hormone balance in the body and helps the body resist infection by producing immune factors. Associated with the liver is the gall bladder that synthesizes bile to assist in the digestion of fat.

The nutrient-rich blood leaving the intestines passes through the liver before transferring to other portions of the body. Thus, the liver is the primary organ that processes the nutrients and other compounds absorbed by the intestines during digestion.

In addition to these "energy" functions, the liver also cleanses toxins from the blood introduced through digestion and breathing. An impaired liver is less able to perform these detox functions or provide the detox functions at optimal levels. In addition to impairment arising from cell damage, over time, the liver tends to decrease in size and blood flow through the liver also decreases—thus reducing the liver's ability to remove toxins and properly regulate body processes.

Substances that are toxic to humans are continually introduced to the body from the environment, and when toxin intake exceeds removal rate, toxins accumulate in the body. The liver, associated gall bladder, and bowel are organs substantially involved in removing toxins. However, in serving their role as toxin eliminators, over time toxins build up in these organs that are either poorly or not eliminated. Thus, while the body may effectively transfer toxins to these organs for excretion and elimination, some types of toxins are poorly excreted and/or eliminated, which results in an increasing habitual toxin concentration in the body.

While many toxins exist, the most problematic toxins for the liver, gall bladder, and bowel to excrete and eliminate arise from heavy metals, mold toxins, and endotoxins. As such toxins are known to concentrate in the liver, gallbladder, and bowel, but are not readily water soluble, drinking copious amounts of water to "flush the system" has little effect. With age, the concentration of such "habitual toxins" in these organs generally increases, even without an acute exposure.

Negative health and disease states are associated with low toxin excretion/elimination performance of the liver, gall bladder, and bowel. Such negative health and disease states in the liver include reduced living cell function and permanent cell damage (cirrhosis). Thus, a global reduction in liver function can arise from the living and productive liver cells operating less efficiently or from permanent damage to a portion of the cells forming the liver. While severe reductions in liver function are readily apparent, including jaundice and chronic vomiting and diarrhea, less severe reductions in liver function leading to fatigue, inefficient fat metabolism, and the resulting obesity, are often ignored.

FIG. 1 represents the conversion, conjugation, excretion, and elimination of toxins from the body. In combination, these processes are often referred to as detoxification. Detoxification occurs in three phases. Phase I conversion reactions involve the oxidation, reduction, and hydrolysis of toxins by enzymes from the cytochrome P450 (CYP450) family of enzymes. These enzymes chemically and irreversibly modify the structure of the toxins through oxidation, reduction, and/or hydrolysis. The intention is to modify the toxins for excretion, but with some toxin forms, the process can convert the toxins into more toxic metabolites, as free radicals are often formed.

Phase II conjugation reactions involve the enzymatic transformation of the Phase I modified toxins into larger, inactive, and water-soluble conjugates that may be excreted. The Phase II transformations include sulfation (transfer of a sulfo-group), glucuronidation (transfer of a glucuronic acid component), and glutathione conjugation (transfer of charged glutathione).

Phase III transport involves moving the Phase II conjugated molecules through cellular membranes, so the molecules may be excreted from the organs into the bowel for elimination. Transportation of the Phase II produced conjugates are affected through multidrug resistance proteins (MRPs 1-4), organic anion transport proteins (OATPs), P-glycoprotein (P-gp), and bile salt export protein (BSEP). MRP1 assists in exporting the Phase II conjugated molecules into the circulation system. The OATPs assist in moving the Phase II conjugated molecules into the liver from the circulation system. MRP2 assists in moving the Phase II conjugated molecules from the liver into the bile canaliculus. The Phase II conjugates reaching the bile canaliculus may be excreted into the small intestine for elimination with assistance of the BSEP.

The literature contains many representations regarding various natural products that may generally improve "liver health". However, the specific blood concentrations of such substances required to have a positive effect on the cells forming the liver and gallbladder, if the substances have a positive effect on the liver and/or gallbladder, is uncertain, especially without IV administration. Furthermore, unless Phases I through III of detoxification can be simultaneously or nearly simultaneously stimulated, the toxins are not excreted. It is believed of little value to stimulate one or two of the three phases in isolation without excretion.

A list of natural products previously reported to provide improvements in the health of the liver follows.

The root of the dandelion plant is reported to have diuretic properties and to prevent damage to the liver while stimulating bile flow from the gallbladder due to the presence of sesquiterpene lactones in the root. Thus, dandelion is reported to stimulate the production of bile by the liver (choleretic), stimulate the flow of bile from the gallbladder into the duodenum (cholagogue), and serve as a diuretic. Dandelion plant extracts also are reported to increase the activity of glutathione (GSH) and GSH-related enzymes in the liver, and the long-chain saccharides present in the root may have anti-inflammatory effects.

Gentian is a bitter herb reported to promote bile flow from the gallbladder. Gentian may also increase the level of glutathione and other antioxidant-supporting enzymes in the liver.

The goldenrod or solidago plant is reported to increase glutathione concentration in the liver.

Myrrh, an oleo gum resin from trees of the *Commiphora* species, is reported to increase bile flow, while also having antifungal, antibacterial, anti-inflammatory, and smooth-muscle relaxing action.

Milk Thistle is reported to have an antioxidant effect attributed to the flavonoid silymarin and to assist in removing heavy metals, alcohol, and pesticides from the liver. The antioxidant effect is believed to protect the outside of cells against oxidative damage and resulting mutation in addition to increasing liver glutathione levels.

R-lipoic acid (RLA) is reported to stimulate rapid liver regeneration in the face of otherwise deadly ingestion of poisonous *amanita* mushrooms when delivered in high doses intravenously (IV). Thus, R-lipoic acid is reported to regenerate damaged liver cells, if sufficient blood concentration is obtained.

Diindolylmethane (DIM) is a compound derived from indole-3-carbinol which is found in cruciferous vegetables such as broccoli, brussels sprouts, cabbage and kale. DIM is reported to induce the antioxidant response element (ARE).

Quercetin is a plant polyphenol from the flavonoid group, found in many fruits, vegetables, leaves, and grains. When IV administered, quercetin acts as an antioxidant by scavenging (deactivating) free radicals, such as oxygen radicals, and as an activator of estrogen receptors. However, the bioavailability of quercetin in humans is low and highly variable (0-50%), and is rapidly cleared with an elimination half-life of 1-2 hours after oral ingestion of quercetin containing foods or supplements. Following dietary ingestion, quercetin undergoes rapid and extensive metabolism that makes the biological effects observed in IV administered studies unlikely to apply to conventional oral administration.

Luteolin is a flavone found in celery, broccoli, green pepper, parsley, thyme, dandelion, perilla, chamomile tea, carrots, olive oil, peppermint, rosemary, navel oranges, and oregano. Plants rich in luteolin have been used in Chinese traditional medicine for treating various diseases such as hypertension, inflammatory disorders, and cancer.

From a detoxification perspective, the following solid binding agents have been reported to assist in removing toxins from the body.

Activated charcoal adsorbs (binds) organic molecules including endotoxins, some pesticides, and some herbicides. It is commonly administered to people who have ingested organic poisons or overdosed on medications in an attempt to bind the poisons/medications before they reach the bloodstream.

Zeolite is often thought of a metal binder, but can also bind some mold toxins and reduce bacterial growth.

Bentonite clay binds aflatoxin, other mold toxins, mycotoxins, such as zearalenone, cyanotoxins from algae, bisphenol-A (BPA), pesticides, herbicides, and some heavy metals. Bentonite clay also binds the heavy metal toxins cadmium and nickel.

Chitosan is sold over the counter to allegedly trap fats and reduce cholesterol. Chitosan is reported to bind bile salts and to bind the toxins excreted in the bile including heavy metals, such as mercury, polychlorinated biphenyls (PCBs), phthalates, and BPA. Chitosan also is reported to bind ochratoxin, a mold toxin, and some endotoxins.

The following have been reported to assist in improving bowel health if consumed as part of the diet.

Acacia Gum is reported to support the health of the cells that form the bowel mucosa.

*Aloe vera* also supports the health of the cells that form the bowel mucosa, but from a lubrication and inflammation reduction perspective.

FIG. 2A and FIG. 2B represent a liposome 200 having a double wall (bilayer) of phospholipids formed from a hydrophilic exterior wall 220 and a hydrophilic interior wall 225. The interior of the double wall 210 is hydrophobic. The hydrophilic interior wall 225 forms a capsule interior 230, to form what may be referred to as a "water-core" liposome. Liposomes may be thought of as small, fluid-filled capsules where the wall of the capsule is formed from two layers of a phospholipid. As phospholipids make up the outer membranes of living cells, the liposome 200 can be thought of as having an outer, permeable membrane wall like a cell, but without a nucleus or the other components of a living cell within the capsule interior 230. The outer and inner walls 220, 225 of the represented liposome 200 are water-soluble, while the interior of the wall 225 is fat-soluble. A common phospholipid used to form liposomes is phosphatidylcholine (PC), a material found in lecithin.

When introduced to the body, liposomes are known to deliver their internal contents to living cells through one of four methods: adsorption, endocytosis, lipid exchange, and fusion. In adsorption, the outer wall of the liposome sticks to the living cell and releases its contents through the outer wall of the living cell into the living cell. In endocytosis, the living cell consumes the liposome, thus bringing the entire liposome into the cell. The cell then dissolves the outer wall of the liposome and releases the liposome contents into the interior of the living cell. In lipid exchange, the liposome opens near the living cell and the living cell takes in the localized high concentration of liposome interior. In fusion, the outer wall of the liposome becomes part of the outer wall of the living cell, thus carrying the contents of the liposome into the enlarged living cell. These pathways allow for a potential 100% transfer of the interior contents of the liposome to the interior of the living cell, if the liposome can be brought sufficiently near the cell and is properly constructed to interact with the living cell.

FIG. 3 represents a flattened side view of the double wall (bilayer) of phospholipids that forms the liposome. The phospholipids have polar, hydrophilic "heads" and less polar, relatively hydrophobic "tails". In this representation, the heads form the top and bottom of the bilayer, with the tails forming the interior middle. Oil-soluble compounds can reside between the top and bottom layers within the interior area occupied by the tails.

FIG. 4 represents a micelle 400 having a single wall of phospholipids (monolayer) forming a hydrophilic exterior 420 and a hydrophobic interior 410 lacking the hydrophilic capsule interior of a liposome. Thus, in relation to a liposome, a micelle lacks a bilayer and does not provide the capsule interior that can contain a water-soluble, hydrophilic core composition. The micelle 400 may be thought of as the outer wall of a liposome without the inner wall providing for a capsule interior. Polyethylene glycol modified vitamin E, such as tocopheryl polyethylene glycol succinate 1000 (TPGS), may be used to form micelles in water as the TPGS has a water-soluble head and an oil-soluble tail.

FIG. 5 represents a monolayer surfactant where the oil component is associated with the hydrophobic tails of a surfactant. In this representation, the surfactant has formed a circular shape, thus encircling the oil component and approximating a relatively large, expanded micelle, but such encircling is not required for the oil component to associate with the hydrophobic tails.

Nutritional supplements are conventionally introduced to the bloodstream in multiple ways. Supplements taken orally are absorbed at different rates due to different factors. For example, on average about 10% to 20% of a solid supplement taken orally is absorbed. This can be increased to about 30% with an orally taken gel capsule, to about 45% with a transdermal patch, and to about 50% with conventional intra-oral (sublingual) administration. Injections provide from approximately 90% to 100% adsorption into the bloodstream, but are uncommonly used for nutritional supplements.

The present invention avoids or ameliorates at least some of the disadvantages of conventional oral supplement preparations intended to enhance liver and toxin excretion performance in a living organism.

SUMMARY

In one aspect, the invention provides an intra-oral, nanoemulsion blend for enhancing liver performance in animals when orally administered. The blend includes at least one monolayer surfactant bound particle, where the at least one monolayer surfactant bound particle includes at least one amphiphilic fat, a polyethylene glycol surfactant, an associating oil, and milk thistle; at least one bilayer liposome, where the at least one bilayer liposome includes the at least one amphiphilic fat and the polyethylene glycol surfactant forming a capsule, where an interior of the capsule includes water, ethanol, and glycerin; and a continuous phase including water, ethanol, and glycerin; where the at least one amphiphilic fat is associated with R-Lipoic acid, the blend is a stable dispersion that is transparent, and the at least one monolayer surfactant bound particle and the at least one bilayer liposome have an average particle diameter from 10 to 100 nanometers as carried by the continuous phase.

In another aspect of the invention, there is an intra-oral, nanoemulsion blend for enhancing liver performance in animals when orally administered. In this aspect, the blend includes a milk thistle, diindolylmethane, quercetin, and luteolin first delivery means for simultaneously delivering milk thistle, diindolylmethane, quercetin, and luteolin to the bloodstream of an animal, where the milk thistle, diindolylmethane, quercetin, and luteolin delivery means includes at least one amphiphilic fat, a polyethylene glycol surfactant, and an associating oil; a myrrh, dandelion, gentian, and goldenrod second delivery means for simultaneously delivering myrrh, dandelion, gentian, and goldenrod to the bloodstream of an animal, where the myrrh, dandelion, gentian, and goldenrod delivery means includes the at least one amphiphilic fat and the polyethylene glycol surfactant; an R-lipoic acid delivery means for delivering R-lipoic acid to the bloodstream of an animal, the R-lipoic acid delivery means including the at least one amphiphilic fat; and a liquid carrying means for carrying the first and second delivery means, where the liquid carrying means includes ethanol and glycerin; where the blend is a stable dispersion that is transparent, and the first delivery means and the second delivery means have an average particle diameter from 10 to 100 nanometers as carried by the liquid carrying means.

In another aspect of the invention, there is a liver detoxification method for an animal that includes holding from 4 to 6 milliliters of a nanoemulsion blend under the tongue of an animal from 30 seconds to 2 minutes, where the nanoemulsion blend includes at least one monolayer surfactant bound particle, where the at least one monolayer surfactant bound particle includes at least one amphiphilic fat, a polyethylene glycol surfactant form, an associating oil, and milk thistle; at least one bilayer liposome, where the at least one bilayer liposome includes the at least one amphiphilic fat and the polyethylene glycol surfactant forming a capsule, where an interior of the capsule includes myrrh dissolved in water, ethanol, and glycerin; and a continuous phase including water, ethanol, and glycerin; where the at least one amphiphilic fat is associated with R-Lipoic acid, the blend is a stable dispersion that is transparent, and the at least one monolayer surfactant bound particle and the at least one bilayer liposome have an average particle diameter from 10 to 100 nanometers as carried by the continuous phase; waiting from approximately 20 minutes to 40 minutes; consuming from 2 to 6 grams of a solid powder toxin binding composition suspended in water, where the solid powder toxin binding composition includes a thiol-functionalized silica binder, a zeolite binder, an activated charcoal binder, a bentonite clay binder, a chitosan binder, a mucosal lining repair agent, and a mucosal lining lubricating agent; and excreting the solid powder toxin binding composition.

In another aspect of the invention, there is a method of making an intra-oral, nanoemulsion blend for enhancing liver performance in animals when orally administered, the method includes forming a mixture including milk thistle extract, an amphiphilic fat including at least 30% by weight phosphatidylcholine, a polyethylene glycol surfactant, an associating oil, glycerin, ethanol, and water to form a first emulsion; forming a mixture including an amphiphilic fat including at least 30% by weight phosphatidylcholine, a polyethylene glycol surfactant, an associating oil, glycerin, ethanol, and water to form a second emulsion including liposomes; combining the first and second emulsions with R-Lipoic acid sodium salt to form a third emulsion; combining the third emulsion with additional ethanol and glycerin to form a fourth emulsion; and adding additional water to the fourth emulsion while stirring at room temperature and pressure.

In another aspect of the invention, there is a solid powder toxin binding composition for irreversibly binding toxins in the bowel, the composition includes a thiol-functionalized silica binder; a zeolite binder; an activated charcoal binder; a bentonite clay binder; a chitosan binder; a mucosal lining repair agent; and a mucosal lining lubricating agent.

In another aspect of the invention, there is an intra-oral nanoemulsion for balancing the histamine response in animals when intra-orally administered, the nanoemulsion includes at least one monolayer surfactant bound particle, where the at least one monolayer surfactant bound particle includes at least one amphiphilic fat, a polyethylene glycol surfactant, an associating oil, diindolylmethane, quercetin, and luteolin; and a continuous phase including glycerin, ethanol, and water; where the nanoemulsion is a stable dispersion that is transparent, and the at least one monolayer surfactant bound particle has an average particle diameter from 10 to 100 nanometers as carried by the continuous phase.

In another aspect of the invention, there is a method of balancing histamine response in an animal, the method including holding from 4 to 6 milliliters of a nanoemulsion under the tongue of an animal from 30 seconds to 2 minutes, where the nanoemulsion includes at least one monolayer surfactant bound particle, where the at least one monolayer surfactant bound particle includes at least one amphiphilic fat, a polyethylene glycol surfactant, an associating oil, diindolylmethane, quercetin, and luteolin; and a continuous phase including glycerin, ethanol, and water; where the nanoemulsion is a stable dispersion that is transparent, and the at least one monolayer surfactant bound particle has an average particle diameter from 10 to 100 nanometers as carried by the continuous phase.

In another aspect of the invention, there is a method of making an intra-oral nanoemulsion for balancing histamine response in animals when orally administered, the method includes forming a mixture including an amphiphilic fat including at least 30% by weight phosphatidylcholine, a polyethylene glycol surfactant, an associating oil, diindolylmethane, quercetin, luteolin, glycerin, ethanol, and water to form a nanoemulsion; and stirring the nanoemulsion at room temperature and pressure to form a stable dispersion that is transparent and has an average particle diameter from 10 to 100 nanometers Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow. The scope of the present invention is defined solely by the appended claims and is not affected by the statements within this summary.

BRIEF DESCRIPTION OF THE FIGURES

The invention can be better understood with reference to the following drawings and description. The components in the figures are not necessarily to scale and are not intended to accurately represent molecules, emphasis instead being placed upon illustrating the principles of the invention.

DETAILED DESCRIPTION

Figure 1:
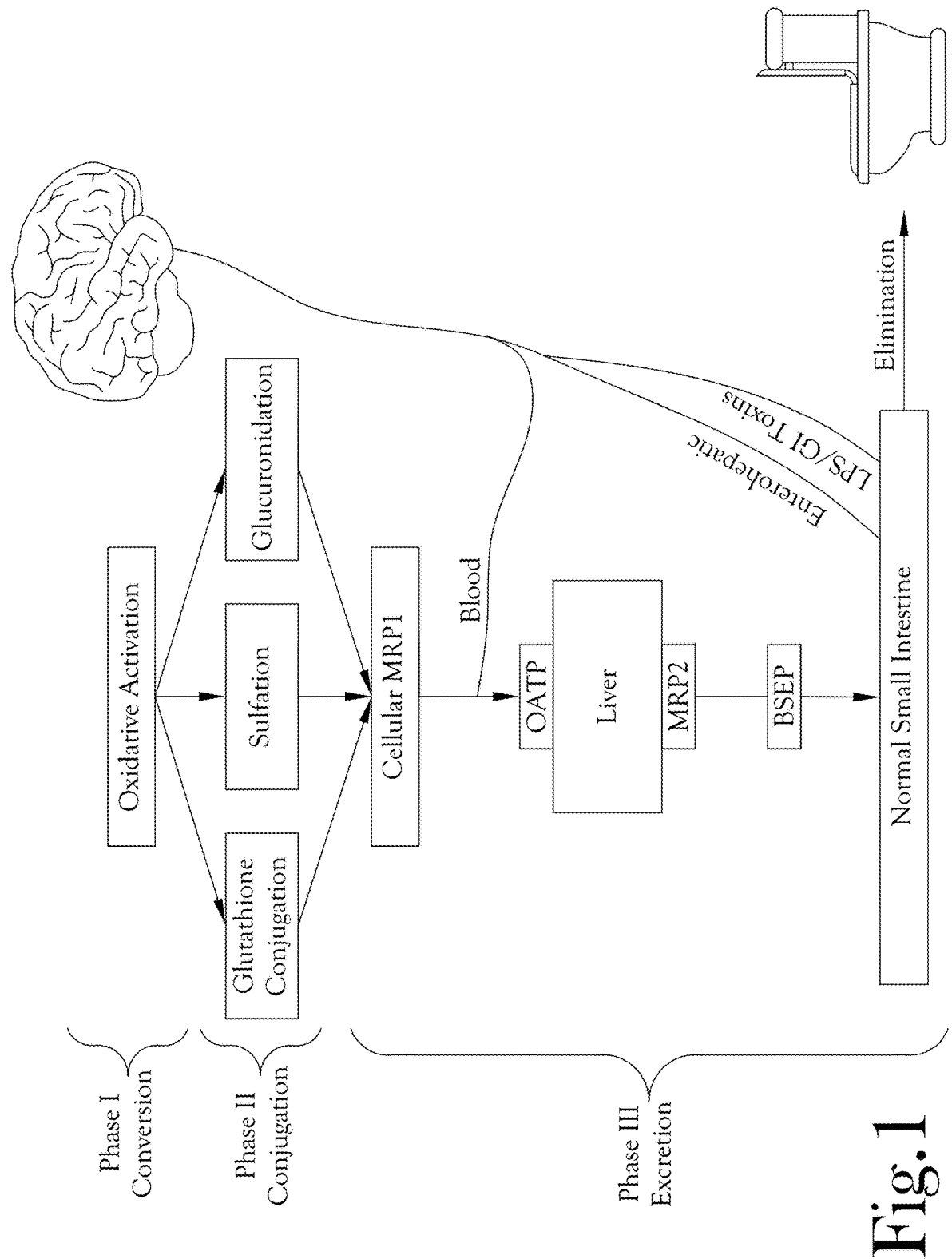
FIG. 1 represents the conversion, conjugation, excretion, and elimination of toxins from the body.
Figure 2A:
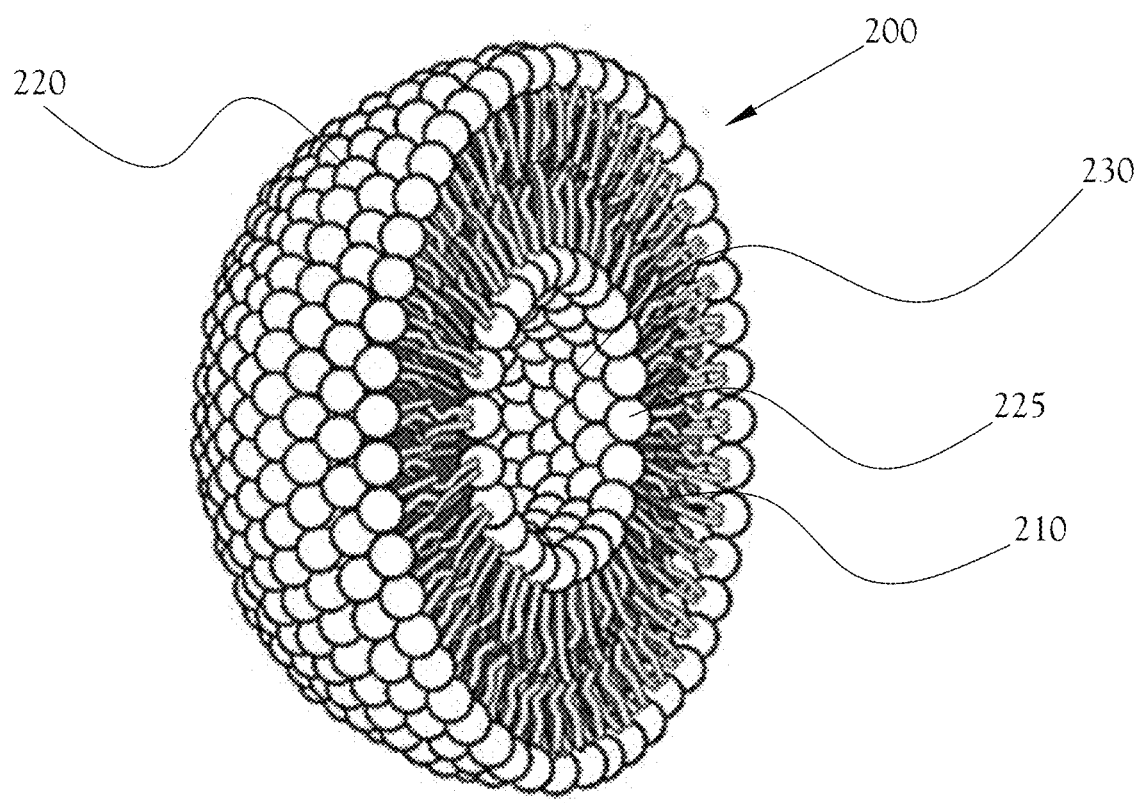
FIG. 2A and FIG. 2B represent a liposome having a double wall of phospholipids forming a hydrophilic exterior and capsule interior with a hydrophobic wall interior.
Figure 2B:
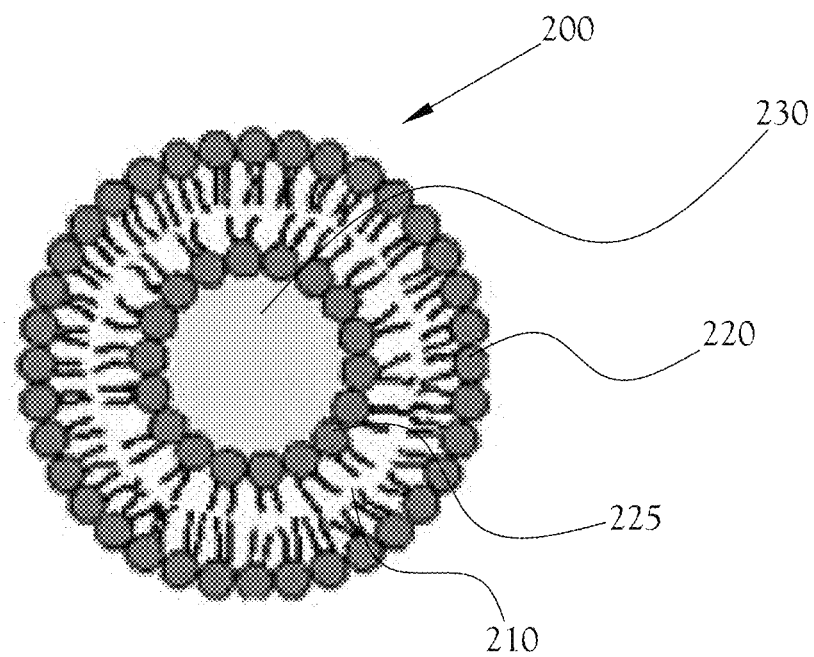
Figure 3:
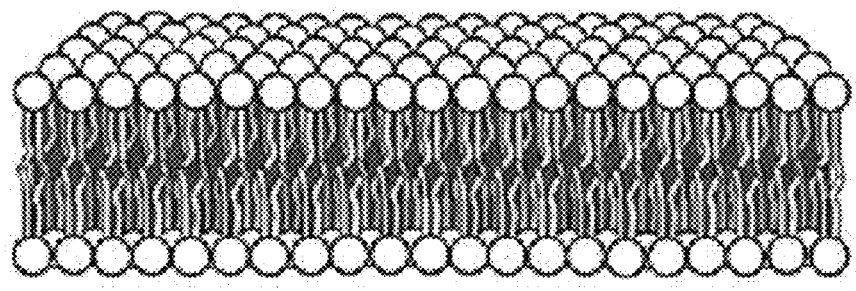
FIG. 3 represents a flattened side view of the double wall (bilayer) of phospholipids that forms the liposome.
Figure 4:
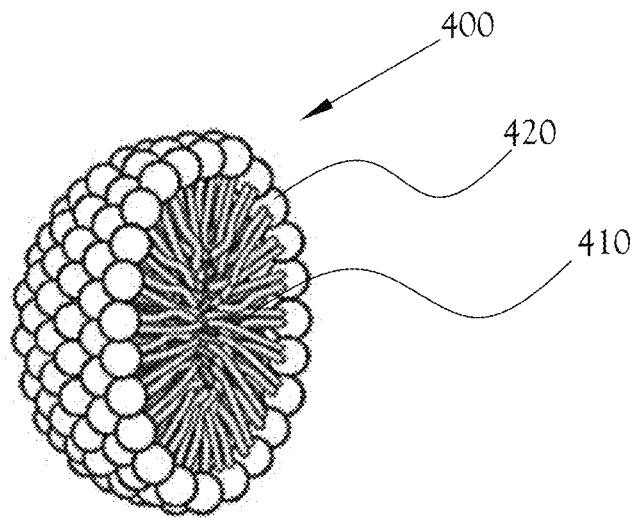
FIG. 4 represents a micelle having a single wall of phospholipids (monolayer) forming a hydrophilic exterior and a hydrophobic interior lacking the capsule interior of a liposome.
Figure 5:
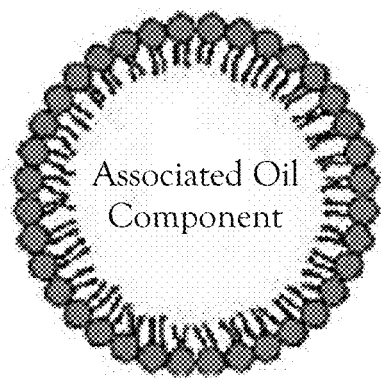
FIG. 5 represents a monolayer surfactant where the oil component is associated with the hydrophobic tails of the surfactant.
Figure 6:
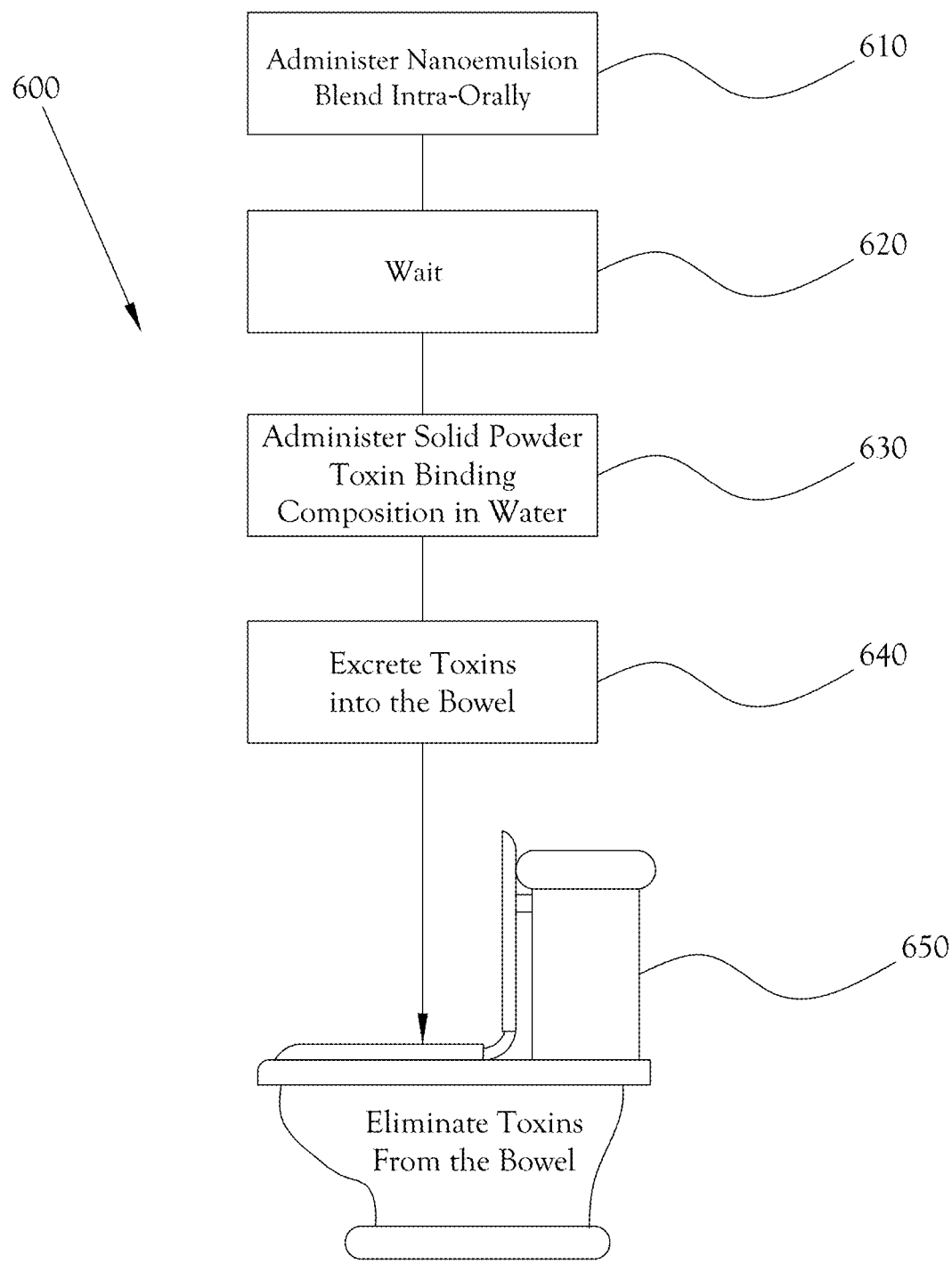
FIG. 6 provides a "push-pull" method of enhancing the excretion of toxins from the liver and irreversibly binding the excreted toxins until elimination.

An intra-oral, nanoemulsion blend is provided that enhances liver and toxin excretion performance in mammals when orally administered. A solid powder toxin binding composition also is provided that may be used to irreversibly bind the toxins reaching the bowel so that once the toxins are excreted into the bowel, they may not be reabsorbed, and are thus eliminated. A method of administering the nanoemulsion blend and the toxin binding composition to enhance toxin excretion also is described. The nanoemulsion blend is ingestible and edible.

The intra-oral, nanoemulsion blend includes at least one monolayer surfactant bound particle first delivery component, at least one bilayer liposome second delivery component, and a continuous phase. The blend optionally may include a micelle as a third delivery component. The monolayer surfactant bound particles, bilayer liposomes, and any optional micelles are held in the continuous phase.

The at least one monolayer surfactant bound particle is an oil-in-water dispersion where the oil of the particle is associated with a surfactant system. The surfactant system of the monolayer surfactant bound particle includes phosphatidylcholine (PC) and tocopheryl polyethylene glycol succinate (TPGS) surfactants. The oil of the at least one monolayer surfactant bound particle includes an associating oil selected from the group consisting essentially of medium chain triglycerides (MCT), citrus oil, and combinations thereof. If the nanoemulsion blend includes the optional micelle, the micelle is primarily formed from PC. The at least one monolayer surfactant bound particle includes a ratio of PC to TPGS from 1:1.8 to 1:3 by weight.

The oil of the monolayer surfactant bound particle includes milk thistle, DIM, quercetin, and luteolin, thus oil-soluble deliverables. The milk thistle is an extract of the milk thistle plant including at least 50% silymarin by weight, and preferably at least 70% silymarin by weight. An oil-soluble tocopherol or tocotrienol (Vitamin E form) also may be included in the oil.

The second delivery component of the nanoemulsion blend is a bilayer liposome originating from PC and TPGS that preferably includes myrrh, gentian, goldenrod, and dandelion root in the capsule interior. By modifying the structure of the PC layers forming the liposome membranes with the TPGS, the liposome may be adapted to include the water, ethanol, and glycerin of the continuous phase so the gentian, goldenrod, dandelion root, and myrrh may be retained in the capsule of the liposome.

Being at least partially soluble in the continuous phase, the gentian, goldenrod, dandelion root, and myrrh may be carried in the continuous phase, associated with the hydrophilic heads of the PC, or preferably carried in the capsule interior of the liposome. When the gentian, goldenrod, dandelion root, and myrrh are carried in the capsule interior of the liposome, the liposome is formed from PC and TPGS, with the TPGS used to alter the nature of the PC membrane.

While having some water solubility, the gentian, goldenrod, dandelion root, and myrrh are believed to have a greater affinity for the polar heads of the PC molecules than water, when combined in water alone. This issue is addressed by the nanoemulsion blend as the interior capsule of the liposome delivery component also includes ethanol and glycerin from the continuous phase, as will be discussed further below, and thus includes a higher concentration of the gentian, goldenrod, dandelion root, and myrrh than possible with a conventional "water-core" liposome. While some portion of the gentian, goldenrod, dandelion root, and myrrh deliverables may be effectively transferred to the bloodstream due to their association with the polar heads of the PC, it is the ability of the liposomes to carry them in their capsule interiors that is believed to provide the substantial enhancement in delivery performance and in solubility of the gentian, goldenrod, dandelion root, and myrrh in a given volume of the nanoemulsion blend.

Whether the particles of the nanoemulsion blend are the monolayer surfactant bound particles or the bilayer liposomes, the R-lipoic acid (RLA) occupies the membranes formed by PC or PC in combination with TPGS. Thus, for the liposomes, the R-lipoic acid occupies the interior of the double wall forming the liposomes, while for micelles and for monolayer surfactant bound particles, the R-lipoic acid associates with the hydrophilic tails. As discussed further below, the nanoemulsion blend allows the gentian, goldenrod, dandelion root, myrrh, milk thistle, quercetin, luteolin, DIM and R-lipoic acid to be transported to the cells of the liver substantially simultaneously and in the desired ratios to maximize liver performance.

Preferably, the nanoemulsion blend has a PC to TPGS ratio from 1:1.6 to 1:3 by weight. Whether the particles of the nanoemulsion blend are monolayer surfactant bound particles, bilayer liposomes, or optional micelles, the particles have an average diameter from 10 to 125 nanometers (nm) or from 10 to 100 nm, preferably from 10 to 80 nm, and more preferably from 10 to 60 nm. The approximately 125-nm average diameter upper limit is important, as particles larger than this will not transport effectively through the tissues of the mouth and enter the bloodstream, but instead will enter the stomach and be substantially irreversibly chemically altered (digested), and thus deactivated, by acid and bile salts. The 100 nm average diameter upper limit provides transparency to the nanoemulsion blend, as larger average particle diameters provide translucent liquids that degrade into milky liquids if unstable. Thus, average particle diameters of 100 nm and less are preferred to provide a nanoemulsion blend that is transparent with optimized intra-oral delivery.

Intra-oral delivery of the liposomes in combination with the monolayer surfactant bound particles enables rapid, and substantially simultaneous intra-oral adsorption of both the water-soluble constituents and of the oil-soluble constituents of the nanoemulsion blend into the bloodstream. Thus, intra-oral delivery of the nanoemulsion blend in combination with the liposome and monolayer surfactant bound particle structures in the continuous phase prevents the extensive metabolism of the supplement constituents of the nanoemulsion blend observed for conventional, orally-administered supplements.

As the supplement constituents of the nanoemulsion blend are transferred intra-orally to the bloodstream without passing through the gut, substantially enhanced bioavailability is achieved. In fact, the liposomes and accompanying monolayer surfactant bound particles of the nanoemulsion blend can approach IV administration in the rate and concentrations at which the body transfers the supplement constituents of the nanoemulsion blend into the bloodstream. As the nanoemulsion blend substantially avoids digestion by the stomach, liver and intestine, the delivered supplement constituents enter the bloodstream substantially unaltered. In addition to the advantages of not requiring venipuncture for relatively rapid and high bloodstream concentration bioavailability, especially in comparison to conventional oral administration techniques, the nanoemulsion blend may maintain a longer-duration increased concentration of the delivered supplement constituents in the bloodstream than available from an IV injection, and thus a longer duration, high-concentration availability to the living cells.

The continuous phase of the nanoemulsion blend includes water, glycerin, and ethanol. The continuous phase of the nanoemulsion blend constitutes from 70% to 90% by weight, preferably from 76% to 85% by weight, and more preferably from 78% to 84% by weight of the nanoemulsion blend, with the remaining weight attributable to the monolayer surfactant bound particles, liposomes, micelles, supplement constituents, and the like. The ethanol is preferably USP food grade 190 proof (95% ethanol, 5% water). If the ethanol includes in excess of 10% water, the additional water should be considered in relation to the total water content of the nanoemulsion blend to prevent precipitation of the oil-soluble deliverables.

The ratio of glycerin to ethanol in the continuous water phase is preferably approximately 1:1 by weight, with deviations for the glycerin and ethanol components up to 20% by weight being included, and with deviations up to 10% by weight being more preferred, thus 1:1±20% by weight or 1:1±10% preferred by weight.

Water is present in an approximately 1:1.5 ratio by weight with the combined glycerin/ethanol, with deviations for each component up to 20% by weight (1:1.5±20%) being included, and with deviations for each component up to 10% by weight (1:1.5±10%) being more preferred. Thus, the ratio of water to glycerin to ethanol is preferably 1:0.75:0.75±20%. The nanoemulsion blend is at least 25% water by weight, preferably at least 30% by weight. The nanoemulsion blend is at least 20% glycerin by weight and at least 20% ethanol by weight.

Other constituents, such as desired flavoring, sodium hydroxide (NaOH), Vitamin E, and acacia gum may be included in the nanoemulsion blend. The other constituents are selected to not interfere with the beneficial operation of the liver performance enhancing supplement constituents or the physical structure of the nanoemulsion blend providing the enhanced delivery and deliverable solubility in relation to conventional systems.

The monolayer surfactant bound particle may be provided in a continuous phase without the liposomes or optional micelles to provide histamine balancing. In this instance, the continuous phase preferably constitutes about 70% by weight of the nanoemulsion, and the ratio of glycerin to ethanol to water is approximately 1.3:1:1.4 with deviations of ±30% or ±20%. In this instance the monolayer surfactant bound particle includes diindolylmethane, quercetin, and luteolin in a ratio of 0.5:0.8:1±20%. The milk thistle is excluded, however, inclusion of a tocopherol or tocotrienol form of Vitamin E is preferred. Vitamin C is preferably included in the continuous phase.

Liver performance, thus the ability as a function of time of the liver and gall bladder to metabolize fats, carbohydrates, protein, and especially stored fat; to remove toxins from the blood; and to excrete toxins, may be adversely affected by habitual toxin build up and aging. Increasing habitual toxin levels within the liver may damage the membranes forming the cells of the liver and/or interfere with the excretion pathways used by the liver to convert, conjugate, and excrete toxins. In addition to increased habitual toxin build up, aging also plays a part in the weakness or deformation of the membranes making up the cells forming the liver.

An enhancement of liver performance is believed attainable through five different pathways. These pathways are biogenesis stimulation, cell protection, reduced toxin leakage, increases in the rate of toxin modification and excretion, and increased bile flow as a function of time.

The first pathway is the stimulation of liver cell biogenesis (enhanced creation rate of new liver cells). By enhancing the rate at which new liver cells are generated, the percentage of the liver cells constituting cells with damaged, weak, and deformed cell membranes may be reduced. Enhancing the production rate of new liver cells may be accomplished by switching on the genes that produce liver cells. R-lipoic acid is believed to enhance the activity of (trigger) the genes that produce liver cells. Thus, delivering more bioavailable and bioactive R-lipoic acid to the cells of the liver is believed to turn on the systems that replace damaged liver cells with new liver cells.

The second pathway to enhanced liver performance is believed attainable through the protection of existing liver and bowel cells from radicals, especially when the radicals arise from toxin and heavy metal catalyzed radical formation. Protecting the existing liver cell membrane structures from radical damage is believed to increase the activity and efficient toxin elimination lifespan of the existing liver cells. Protecting the existing liver cells from radicals may be accomplished by stimulating the production of Nrf2, a nuclear transcription factor. Nrf2 production is known to decline with age, providing one reason the elderly are more susceptible to toxins. For example, elevated habitual concentrations of Ochratoxin-A, a common mold toxin, and Indoxyl sulfate, a toxin associated with the heavy metal cadmium, are both believed to act as Nrf2 inhibitors.

Nrf2 can activate the genes that increase the production of glutathione (GSH) and radical control enzymes (antioxidant response element—ARE) by the cells—in combination, the inherent oxygen radical protection system of the liver. GSH can protect cells against damage from oxygen radicals, peroxides, lipid peroxides, and heavy metals through either direct reduction or by maintaining antioxidants, such as Vitamin C and Vitamin E, in their active (reduced) form. However, as glutathione is lost during the removal and elimination of mercury and other toxins from the cells, glutathione can become depleted during the Phase III of detoxification without supplementation.

A synergistic combination of milk thistle, R-lipoic acid, DIM and quercetin is believed to stimulate the existing liver cells to increase production of Nrf2. The lack of such substantially simultaneous delivery in sufficient concentration (bioavailability) and ratio of the milk thistle, R-lipoic acid, DIM and quercetin to the cells of the liver is believed to explain some of the inconsistent results observed in the literature for these supplements in isolation or in improper ratio. Preferably, the ratio of milk thistle to R-lipoic acid to DIM to quercetin is 1:4:1:0.6 by weight, with deviations for each component up to 10% by weight being included, and with deviations for each component of up to 5% by weight being preferred, thus 1:4:1:0.6±10% by weight or 1:4:1:0.6±5% preferred by weight.

To achieve these desired ratios at the cellular level, the transport of the multiple supplement constituents should be controlled from introduction to the body until the supplements reach the interior of the liver cells. Without the nanoemulsion blend, the body will alter the concentration and ratios of the supplement constituents inconsistently with each introduction.

The third pathway is through a reduction in toxin leakage from the liver and bowel. Leakage occurs from inflammation of the liver and bowel that opens pathways between the cells forming the organs. During toxin elimination, it also is especially advantageous to reduce the permeability of the bowel to toxins. By reducing the ability of toxins to escape these organs, toxin re-entry to the bloodstream may be reduced. Otherwise, toxins leaving the liver or entering the bowel at an enhanced rate will eventually enter the bloodstream and be returned to the liver. Reducing toxin leakage may be accomplished by reducing inflammation and by reducing bowel permeability.

Inflammation of the liver may be reduced or prevented by a synergistic combination of DIM, quercetin, and luteolin. The lack of such substantially simultaneous delivery in sufficient concentration (bioavailability) and ratio of the DIM, quercetin, and luteolin to the cells of the liver is believed to explain some of the inconsistent results observed in the literature for these supplements in isolation or in improper ratio. Preferably the ratio of DIM to quercetin to luteolin is 1:0.6:0.6 by weight, with deviations for each component up to 10% by weight being included, and with deviations for each component of up to 5% by weight being preferred, thus 1:0.6:0.6±10% by weight or 1:0.6:0.6±5% preferred by weight. Furthermore, bowel permeability to toxins may be reduced by the quercetin component of this combination. Thus, the quercetin component of this combination is believed to reduce inflammation in the liver, while also reducing bowel permeability to toxins.

To achieve these desired ratios at the cellular level, the transport of the multiple supplement constituents should be controlled from introduction to the body until the supplements reach the interior of the liver cells. Without the nanoemulsion blend, the body will alter the concentration and ratios of the supplement constituents inconsistently with each introduction.

The fourth, and likely most important, pathway to enhanced liver performance is more complex, requiring an enhancement in the rate existing liver cells can modify and excrete toxins into the bowel. In relation to FIG. 1, toxin modification occurs in Phases I and II, while the excretion of toxins into the bowel occurs in Phase III.

Enhancing the rate at which liver cells can convert toxins in Phase I may be accomplished by increasing the activity as a function of time of the enzymes from the cytochrome P450 (CYP450) family of enzymes. Such oxidation, reduction, and/or hydrolysis within the liver is believed promoted by the synergistic and substantially simultaneous delivery of milk thistle and dandelion to the cells of the liver. As milk thistle is more hydrophobic than dandelion, the lack of such substantially simultaneous delivery in sufficient concentration (bioavailability) and ratio of the milk thistle and dandelion to the cells of the liver is believed to explain some of the inconsistent results observed in the literature for these supplements in isolation or in improper ratio or delivery. Preferably the ratio of milk thistle to dandelion is 1:20 by weight, with deviations for each component up to 10% by weight being included, and with deviations for each component of up to 5% by weight being preferred, thus 1:20±10% by weight or 1:20±5% preferred by weight.

Enhancing the rate at which liver cells can conjugate converted toxins in Phase II, thus enzymatic conjugation reactions, may be accomplished by increasing the activity as a function of time of the enzymes that catalyze the sulfation, glucuronidation, and glutathione conjugation conversion reactions within the liver. The combination of the R-lipoic acid, DIM, and quercetin are believed to stimulate Nrf2, a nuclear transcription factor. Nrf2 can activate the genes that increase the production of antioxidants by the cells and that increase the production of enzymes involved in the conjugation reactions within the liver. Nrf2 stimulation and the associated increase of conjugation enzymes within the liver is believed promoted by the synergistic and substantially simultaneous delivery of R-lipoic acid, DIM, and quercetin to the cells of the liver. The lack of such substantially simultaneous delivery in sufficient concentration (bioavailability) and ratio of the R-lipoic acid, DIM, and quercetin to the cells of the liver is believed to explain some of the inconsistent results observed in the literature for these supplements in isolation or in improper ratio. Preferably the ratio of R-lipoic acid to DIM to quercetin is 4:1:0.6 by weight, with deviations for each component up to 10% by weight being included, and with deviations for each component of up to 5% by weight being preferred, thus 4:1:0.6±10% by weight or 4:1:0.6±5% preferred by weight.

Enhancing the rate at which liver cells can excrete toxins, thus eliminating conjugated toxins to the bowel, may be accomplished by enhancing the transcription and stabilization of Phase III transporters, most importantly bile salt export protein (BSEP), and the multi-drug resistance protein 2 (MRP2) to increase production of bile by the liver and to increase bile flow from the gallbladder. Such transcription and stabilization enhancement of the Phase III transporters is believed to provide an increase in BSEP and MRP2 activity within the liver. Thus, the synergistic and substantially simultaneous delivery of milk thistle and myrrh to the cells of the liver is believed to enhance the transcription and stabilization of BSEP and MRP2 to increase toxin excretion from the liver. As myrrh is more hydrophobic than milk thistle, the lack of such substantially simultaneous delivery in sufficient concentration (bioavailability) and ratio of the milk thistle and myrrh to the cells of the liver is believed to explain some of the inconsistent results observed in the literature for these supplements in isolation or in improper ratio or delivery. Without the ability of the nanoemulsion blend to deliver both more and less hydrophobic supplement constituents substantially simultaneously, these two supplement constituents could not be delivered orally and maintain the desired ratios. Preferably the ratio of milk thistle to myrrh is 1:4 by weight, with deviations for each component up to 10% by weight being included, and with deviations for each component of up to 5% by weight being preferred, thus 1:4±10% by weight or 1:4±5% preferred by weight.

To achieve these desired ratios at the cellular level, the transport of the multiple supplement constituents should be controlled from introduction to the body until the supplements reach the interior of the liver cells. Without the nanoemulsion blend, the body will alter the ratios of the supplement constituents inconsistently with each introduction.

The fifth pathway to enhanced liver performance results from an increase in bile flow. The greater the bile flow as a function of time, the higher the likelihood that excreted toxins will be eliminated and not retained in the organs or lost to the bloodstream. Increasing bile flow may be accomplished with one or more supplement constituent. Preferable flow increasing supplement constituents include dandelion, gentian, and goldenrod, but other supplement constituents having bile flow increasing effects may be used. Gentian is a preferred bile flow increasing supplement constituent as it may also have a GSH increasing effect in the liver. However, the synergistic and substantially simultaneous delivery of dandelion, gentian, and goldenrod to the cells of the liver is believed to enhance bile flow in relation to gentian alone. The lack of such substantially simultaneous delivery in sufficient concentration (bioavailability) and ratio of the dandelion, gentian, and goldenrod to the cells of the liver is believed to explain some of the inconsistent results observed in the literature for these supplements in isolation or in improper ratio. A preferable ratio of dandelion to gentian to goldenrod is 10:3:5 by weight, with deviations for each component up to 20% by weight being included, and with deviations for each component of up to 10% by weight being preferred, thus 10:3:5±20% by weight or 10:3:5±10% preferred by weight.

To achieve these desired ratios at the cellular level, the transport of the multiple supplement constituents should be controlled from introduction to the body until the supplements reach the interior of the liver cells. Without the nanoemulsion blend, the body will alter the ratios of the supplement constituents inconsistently with each introduction. For example, without the nanoemulsion blend, oral administration would not allow substantially simultaneous delivery of the preferred 1:4:4 ratio by weight of milk thistle to myrrh to R-lipoic acid to the liver cells with deviations for each component of up to 10% by weight being included, and with deviations for each component of up to 5% by weight being preferred, thus 1:4:4±10% by weight or 1:4:4±5% preferred by weight.

Intra-oral delivery with the nanoemulsion blend including the R-lipoic acid provided by the PC and TPGS structures in the continuous phase prevents the extensive metabolism of the R-lipoic acid observed for conventional oral administration. As the oil-soluble milk thistle is used with the less oil-soluble myrrh, dandelion, gentian, and goldenrod, the PC and TPGS allows the desired ratio of each supplement constituent to reach the liver substantially simultaneously, which as with the highly metabolized R-lipoic acid, does not occur with conventional oral delivery. While some beneficial effect may be possible regarding liver and bowel cell membrane protection from the TPGS directly, the oil-soluble tocotrienol forms are believed to more readily provide the desired concentration and combination of milk thistle/DIM/R-lipoic acid within these organs in relation to the other components of the nanoemulsion blend.

Furthermore, without the combination of the monolayer surfactant bound particle to carry the oil-soluble deliverables in combination with the constituents of the continuous phase and the bilayer liposomes having capsule interiors including the continuous phase to carry the gentian, goldenrod, dandelion root, and myrrh deliverables, the blood delivery performance, transparency, and stable dispersion of the nanoemulsion blend could not be achieved. The fact that the nanoemulsion blend forms a transparent, stable dispersion that also includes R-lipoic acid is quite unexpected.

From a liver performance enhancement perspective, the PC in the nanoemulsion blend may increase the health of the existing liver cells by replacing phospholipids lost from the membranes forming the physical structures of the liver cells. Liver cells continually lose phospholipids to the bile flow due to MDR transport. Unless replenished at or in excess of the loss rate to the bile flow, the reduced phospholipid concentration in the liver cell membranes results in damaged or "aged" cell membranes and thus less healthy liver cells. The PC of the nanoemulsion blend is believed to prevent and to some degree reverse the reduction in liver performance resulting from the loss of phospholipids from the liver cell membranes. The TPGS of the particle and lipid components of the nanoemulsion blend may provide additional anti-oxidant benefits to the liver cells; however, the supplement constituents are believed to provide the primary anti-oxidant benefit.

The nanoemulsion blend enhances liver performance through multiple pathways, as previously discussed. However, increased toxin modification and excretion coupled with increased bile flow increases toxin concentration in the bowel. When the toxins are excreted into the bowel, some toxins, especially those arising from mold, are often reabsorbed by the bowel and transferred back to the bloodstream before the toxins are eliminated, thus creating a "toxin catch-22" situation. Such toxin readsorption from the bowel and into the bloodstream is believed to negate a portion of the benefit provided by the enhanced toxin modification, toxin excretion, and bile flow provided by the nanoemulsion blend as heightened toxin excretion from the liver lacks benefit if the excreted toxins are then reabsorbed, and thus not eliminated from the body.

To reduce toxin readsorption, a solid powder toxin binding composition may be used to irreversibly bind the toxins reaching the bowel so that once the toxins are excreted into the bowel, they are not reabsorbed, and are thus eliminated. However, as the toxins entering the bowel are of diverse form, a single binder is inadequate. Furthermore, as the binding agents are solids in powder form that do not dissolve as they pass through the bowel, the mucosal lining of the bowel could sustain abrasion damage from the solid powder binding agents if the lining is not adequately protected. Thus, the toxin binding composition also includes protective agents that may assist in repairing, lubricating, and reducing inflammation of the mucosal lining.

The toxin binding composition preferably includes at least five binding agents, at least one agent to repair the mucosa of the bowel, and at least one agent to provide additional lubrication of the mucosal wall and an anti-inflammatory effect. While the lubrication, repair, and anti-inflammatory agents (in combination "LRA agents") could be provided in a different physical form and/or separated from the binding agents, the LRA agents are preferably in powder form and combined with the powder form binding agents. This combination is preferred as an object of the toxin binding composition is to provide the LRA agents to the mucosal lining of the bowel substantially simultaneously with the binding agents so the benefits of the LRA agents to the mucosal lining is provided when the potentially abrasive binding agents are present in the bowel.

The at least five binding agents include a thiol-functionalized silica, a zeolite, activated charcoal, bentonite clay, and chitosan. The thiol-functionalized silica is optimized to irreversibly bind heavy metals, specifically lead, mercury, cadmium, and arsenic. Importantly, the thiol-functionalized silica can bind methyl mercury, an especially difficult form of heavy metal toxin to remove from the body. The thiol-functionalized silica preferably is made by covalently binding aliphatic thiols to silica gel particles. While the bentonite clay and chitosan binding agents can bind some heavy metals to some degree, neither bind heavy metals irreversibly in relation to body processes. Hence, the thiol-functionalized silica is substantially more effective for irreversibly binding alkyl mercury complexes.

The zeolite irreversibly binds some metals, but is believed to make a significant contribution to the binding of mold toxins. The activated charcoal irreversibly binds to many organic molecules, specifically endotoxins, pesticides, herbicides, and some mold toxins. The bentonite clay irreversibly binds to the mold toxin aflatoxin as well as other mold toxins. The bentonite clay is preferably an ultrafine USP grade sodium bentonite clay. The chitosan is provided as a form of "catch all" binder as the chitosan binds with the bile itself. The chitosan may also bind polychlorinated biphenyls (PCBs), phthalates and bisphenol-A (BPA). However, as the chitosan directly binds with the bile excreted from the gall bladder, the chitosan can tie-up toxins in the bile that may or may not be irreversibly bound by the other binding agents.

The repair function of the toxin binding composition is preferably provided by acacia gum. The acacia gum is believed to support the health of the cells that form the bowel mucosa, thus helping to ensure that any damage to the mucosa caused by contact with the solid binding agents is readily repaired. For example, Fibregum™ brand acacia gum, as available from Nexira, France, may be used to provide the repair function to the mucosal membrane of the bowel. While the lubrication and anti-inflammatory functions may be provided by multiple agents, preferably *Aloe vera* is used to provide both functions with a single agent. For example, BiAloe™ brand *Aloe vera*, as available from Lorand Laboratories, Houston, Tex., may be used to provide both lubrication and an anti-inflammatory effect to the mucosal membrane of the bowel.

Preferably, for the binding agents, the ratio of thiol-functionalized silica to zeolite to activated charcoal to bentonite clay, to chitosan is 1:5-20:20-30:0.0002-2:8-20 by weight, with deviations for each component up to 10% by weight being included, and with deviations for each component of up to 5% by weight being preferred, thus 1:5-20:20-30:0.0002-2:8-20±10% by weight or 1:5-20:20-30:0.0002-2:8-20±5% preferred by weight. More preferably, for the binding agents, the ratio of thiol-functionalized silica to zeolite to activated charcoal to bentonite clay, to chitosan is 1:7:30:0.0002:20 by weight, with deviations for each component up to 10% by weight being included, and with deviations for each component of up to 5% by weight being preferred, thus 1:7:30:0.0002:20±10% by weight or 1:7:30:0.0002:20±5% preferred by weight.

Preferably, for the LRA agents, the ratio of thiol-functionalized silica to acacia gum to *Aloe vera* is 1:20-50:1.5-2 by weight, with deviations for each component up to 10% by weight being included, and with deviations for each component of up to 5% by weight being preferred, thus 1:20-50:1.5-2±10% by weight or 1:20-50:1.5-2±5% preferred by weight. More preferably, for the LRA agents, the ratio of thiol-functionalized silica to acacia gum to *Aloe vera* is 1:20:1.6 by weight, with deviations for each component up to 10% by weight being included, and with deviations for each component of up to 5% by weight being preferred, thus 1:20:1.6±10% by weight or 1:20:1.6±5% preferred by weight.

The average particle diameter of the solid powder granules of the toxin binding composition are from 3 to 5 microns. While other average diameters are possible, this range provides optimal suspension in water and toxin adsorption.

FIG. 5 provides a "push-pull" method 500 of enhancing the excretion of toxins from the liver and irreversibly binding the excreted toxins until elimination. The nanoemulsion blend provides the "push", while the toxin binding composition provides the "pull".

In 510, from 3 to 7 mL, preferably from 4 to 6 mL of the nanoemulsion blend is intra-orally administered at least 20 minutes before a meal or at least 20 minutes after eating. While a larger dose of the nanoemulsion blend may be administered, diminishing returns may be observed. The nanoemulsion blend is preferably held under the tongue from 30 seconds to 2 minutes before swallowing to maximize intra-oral adsorption. Shorter and longer intra-oral adsorption time periods may be used, but substantially decrease toxin excretion or provide little additional increase in toxin excretion, respectively.

In 520, nothing other that water is consumed for a wait time from approximately 20 minutes to 40 minutes. While other wait times may be used, shorter or longer wait times decrease the likelihood that excreted toxins will be bound as the availability of the toxin binding composition will not correlate as well with the time of maximum toxin excretion by the liver.

In 530, from 2 to 15 grams, preferably from 4 to 12 grams (approximately 1 to 3 teaspoons) of the solid powder toxin binding composition suspended in water are consumed. A suitable amount of water is 300 mL; however, less or greater amounts of water may be used. While the toxin binding composition does not dissolve in the water, the from 3- to 5-micron average particle diameter of the powder granules allows for suspension.

In 540, toxins excreted from the liver and gallbladder into the bowel are irreversibly bound to the binding agents present in the bowel while the LRA agents protect the mucosal wall of the bowel from abrasion by the binding agents and reduce inflammation and the likelihood that toxins will permeate through the bowel for readsorption by the blood. Additionally, the chitosan binding agent adsorbs bile and toxins present in the bile.

In 550, the binding agents and bound toxins are eliminated from the body.

The following examples illustrate one or more preferred embodiments of the invention. Numerous variations may be made to the following examples that lie within the scope of the invention.

EXAMPLES

Example 1: Constituents of the Intra-Oral, Nanoemulsion Blend

A nanoemulsion blend was prepared having a 5 mL total volume. The blend included approximately 20 mg of DIM, approximately 20 mg of milk thistle extract including approximately 80% silymarin, approximately 10 mg of anhydrous quercetin, approximately 10 mg of luteolin extract, approximately 35 mg acacia, approximately 75 mg of myrrh oleo-gum-resin extract, approximately 375 mg dandelion root extract, approximately 112 mg gentian root extract, approximately 187 mg goldenrod extract, and approximately 75 mg of the sodium salt of R-Lipoic acid by weight. The myrrh, dandelion, gentian, and goldenrod were extracts in water/ethanol having an herb strength of approximately 1:5 herb to the water/ethanol solvent. The blend also included approximately 100 to 200 mg of PC, approximately 700 to 1300 mg ethanol, approximately 1000 to 1600 mg glycerin, and minor amounts of flavoring. TPGS was included to provide the desired physical structures in the nanoemulsion. In addition to these ingredients, the blend included enough water to provide a total volume of 5 mL.

Example 2: A Method of Making an Intra-Oral, Nanoemulsion Blend

The liposome of the nanoemulsion blend was made by combining approximately 8 mg acacia gum, 2 mL liquid myrrh extract, approximately 7 mL liquid dandelion root extract, approximately 3 mL liquid gentian root extract, and approximately 4 mL goldenrod extract in associating oil and ethanol. The combination was then combined with PC, TPGS, glycerin, and water. The combination was then mixed to form a first emulsion.

The monolayer surfactant bound particle of the nanoemulsion blend was made by combining approximately 4 mg DIM, 4 mg milk thistle extract including approximately 80% silymarin, 3 mg quercetin anhydrous, and 3 mg luteolin extract in associating oil and ethanol. The combination was then combined with PC, TPGS, glycerin, and water. The combination was then mixed to form a second emulsion.

The first and second emulsions were combined and approximately 15 mg of R-Lipoic acid sodium salt was then added to the combined emulsions. The resulting combination was then mixed until the R-lipoic acid salt was dissolved to form a third emulsion.

To the third emulsion was added approximately 4 mg of ethanol and approximately 8 mg of glycerin. This combination was then mixed to form a fourth emulsion.

The total volume of the fourth emulsion was then increased to approximately 5 mL with water. Mixing was performed in a mechanically stirred vessel.

Example 3: Constituents of the Solid Powder Toxin Binding Composition

An approximately four-gram serving of the solid powder toxin binding composition was made by combining approximately 700 mg of powdered zeolite, approximately 780 mg of powdered activated carbon, approximately 300 mg of chitosan, approximately 80 mg of *Aloe*, approximately 40 mg of thiol-functionalized silica, approximately 2 g of acacia gum, and approximately 80 mg of sodium bentonite in a mechanical mixer. The mixer was operated to fully combine the different powders.

Example 4: Liver Detox Treatment

A urine sample from a human test subject was analyzed for the mold toxins Ochratoxin A, Aflatoxin Group (B1, B2, G1, G2), Trichothecene Group (Macrocyclic), and Gliotoxin Derivative. The sample was determined to include approximately 10 parts-per-billion (ppb) Ochratoxin A, approximately 1.8 ppb Aflatoxins, no appreciable Trichothecene, and approximately 6.2 ppb Gliotoxins.

The following protocol was then administered daily to the human test subject for approximately two months. On an empty stomach, the human subject placed 5 mL of the nanoemulsion blend under the tongue. The blend was held under the tongue for approximately 30 seconds to 2 minutes before swallowing. The subject then consumed approximately 250 mL of water. Approximately 30 minutes passed, and the subject then consumed 4 grams of the solid powder toxin binding composition suspended in water.

After the two-month protocol period, a second urine sample was analyzed for the mold toxins. The sample was determined to include approximately 0.9 ppb Ochratoxin A, approximately 0.5 ppb Aflatoxins, no appreciable Trichothecene, and no appreciable Gliotoxins. Thus, the nanoemulsion blend provided a greater than 90% (0.5/10*100) reduction in Ochratoxin A, a greater than 70% (0.5/1.8*100) reduction in Aflatoxins, and something approaching a 100% (0/6.2*100) reduction in Gliotoxins. These results demonstrate the ability of the nanoemulsion blend in combination with the solid powder toxin binding composition to reduce the concentration of mold toxins in a human text subject. The protocol would be expected to perform similarly in lower mammals.

Example 5: Bioavailability Uptake and Duration

On an empty stomach, a human subject placed 5 mL of a nanoemulsion including a water-soluble vitamin under the tongue. The nanoemulsion included a bilayer liposome as previously described in the context of the nanoemulsion blend including PC and TPGS including the water-soluble vitamin and a continuous phase. While not identical to the nanoemulsion blend providing enhanced liver performance as previously discussed, it is believed that the bioavailability of oil-soluble components via the previously discussed monolayer surfactant bound particle would be comparable to the bioavailability provided by the bilayer liposome to the water-soluble vitamin.

The nanoemulsion was held under the tongue for approximately 30 seconds to 2 minutes before swallowing. Blood samples were collected before the nanoemulsion was administered and at varying time intervals between 5 and 50 minutes after administration of the nanoemulsion for approximately 4 hours. This procedure was repeated for the water-soluble vitamin in approximately 5 mL of water and for the water-soluble vitamin in a conventional amphiphilic fat-based liposome lacking TPGS. The collected blood samples were analyzed for the concentration of the water-soluble vitamin.

Figure 7:
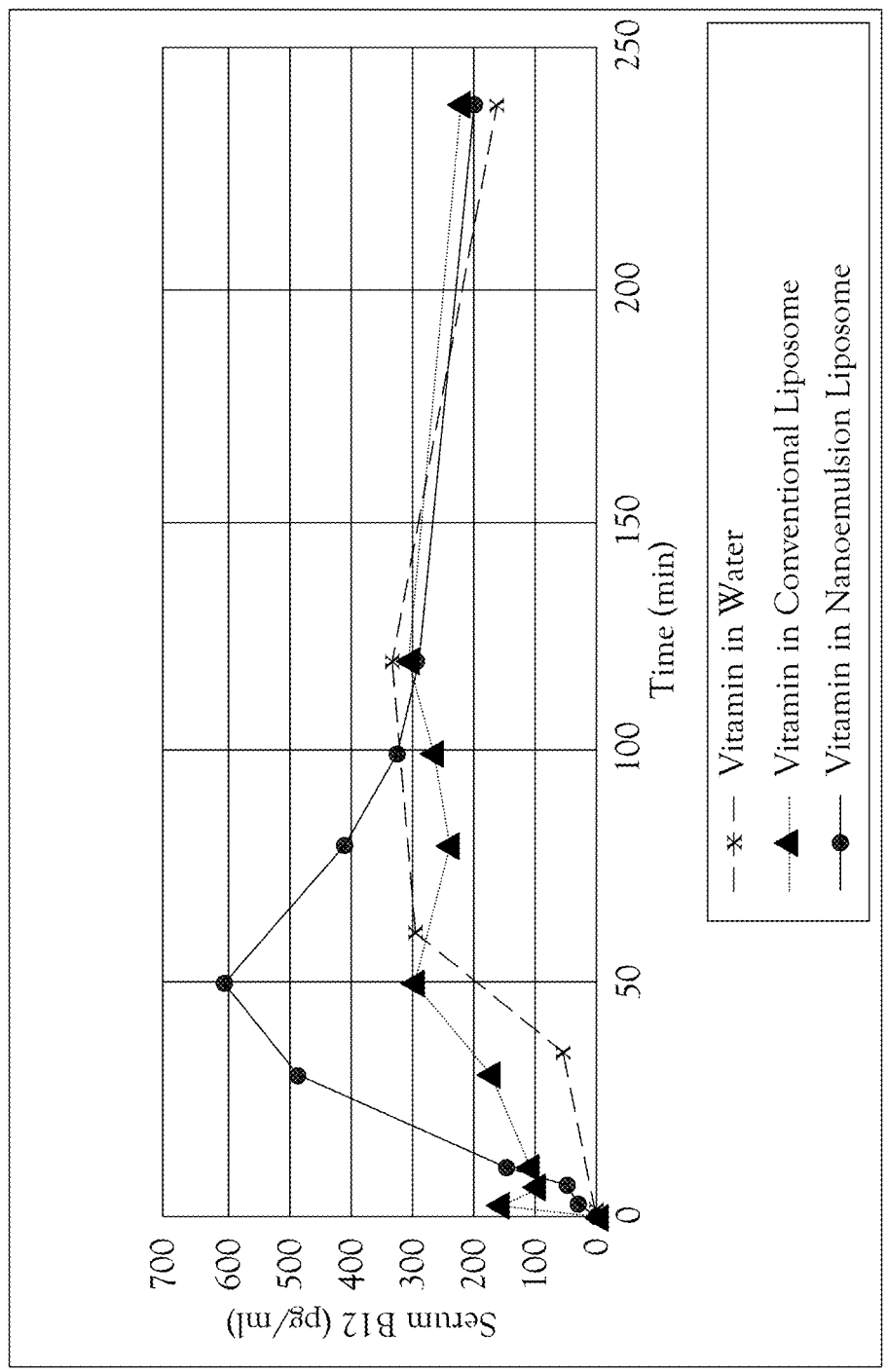
FIG. 7 provides the results of a bioavailability duration analysis in graphical form.

FIG. 7 provides the results of the bioavailability uptake and duration analysis in graphical form. The comparative data establishes that the nanoemulsion administration provides an approximate doubling of the blood concentration of the water-soluble vitamin 50-minutes post administration in relation to the water and conventional amphiphilic fat-based liposome administered vitamin. In addition to the initial and rapid uptake doubling, the blood concentration of the water-soluble vitamin provided by the nanoemulsion remains substantially above the water and conventional amphiphilic fat-based liposome administered blood concentrations until approximately 100-minutes post administration. Thus, establishing the ability of the nanoemulsion to provide supplement constitute blood concentrations approaching 100% greater than those provided by conventional oral administration methods.

Preferably, 4 to 6 mL of the nanoemulsion blend held under the tongue from 30 seconds to 2 minutes provides an at least 400 picograms per milliliter (pg/mL) concentration of the bilayer liposome deliverables in the blood within 40 to 60 minutes of administration to human subjects weighing from 50 kg to 90 kg. More preferably, 4 to 6 mL of the nanoemulsion blend held under the tongue from 30 seconds to 2 minutes provides an at least 500 pg/mL concentration of the bilayer liposome deliverables in the blood within 40 to 60 minutes of administration to human subjects weighing from 50 kg to 90 kg. A similar blood delivery profile is also believed obtained for the monolayer surfactant bound particle deliverables.

To provide a clear and more consistent understanding of the specification and claims of this application, the following definitions are provided.

Intra-oral delivery means that at least 40%, preferably 60%, and more preferably 80% and above of the delivery into the bloodstream that occurs upon oral administration of the liquid including the deliverable occurs by transmucosal absorption through the mouth, throat and esophagus before the liquid reaches the stomach. For particles to be considered suitable for intra-oral delivery, the average particle diameter is at most 125 nm and preferably less than 80 nm. For example, particles having an average diameter of 100 would have only an approximately 40% delivery to the bloodstream intra-orally, while particles having an average diameter of 75 nm would have and approximate 60% intra-oral delivery to the bloodstream. An 80% or greater intra-oral delivery to the bloodstream may be achieved with an average particle diameter of approximately 50 nm in 0.5 mL liquid after a mouth-residency time of 2 minutes.

Solutions lack an identifiable interface between the solubilized molecules and the solvent. In solutions, the solubilized molecules are in direct contact with the solvent.

Liquids are substances that are not a solid or a gas at room temperature and pressure. A liquid is an incompressible substance that flows to take on the shape of its container.

Emulsions are mixtures of two or more liquids that do not solubilize. Thus, one of the liquids carries isolated particles in the form of droplets of the other liquid. The particles of one liquid may be said to be dispersed in the continuous phase of the other liquid. An interface, separation, or boundary layer exists between the two liquids, thus between the continuous phase and the particles. Emulsions may be macroemulsions, pseudo-emulsions, microemulsions, or nanoemulsions. The primary difference between the types of emulsions is the size (average diameter) of the particles dispersed in the continuous phase. Macroemulsions and pseudo-emulsions have average particle diameters from 1 to 20 micrometers.

A stable dispersion may be determined in one of two ways. One way to establish that a dispersion stored in a sealed container substantially excluding air and moisture is stable is when the oil phase particles in a continuous phase do not change in average diameter by more than +/−20% at about 25° C. for a time period of 3 months to 3 years, preferably for a time period of 6 months to 3 years, and more preferably, for a time period of 1 year to 3 years. Another way to establish that a dispersion is stable is when the oil phase particles in the continuous phase do not separate into a visibly distinct phase with a visible meniscus when stored in a sealed container substantially excluding air and moisture at about 25° C. for a time period of 6 months to 3 years, and more preferably, for a time period of 1 year to 3 years. A dispersion is stable if it meets either or both of these criteria.

Average particle diameter is determined by dynamic light scattering (DLS), sometimes referred to as photon correlation spectroscopy. The determination is made between 20 and 25 degrees Celsius. One example of an instrument suitable for average particle diameter determination is a Nicomp 380 ZLS particle sizer as available from Particle Sizing Systems, Port Richey, Fla. DLS can determine the diameter of particles in a liquid by measuring the intensity of light scattered from the particles to a detector over time. As the particles move due to Brownian motion the light scattered from two or more particles constructively or destructively interferes at the detector. By calculating the autocorrelation function of the light intensity and assuming a particle distribution, it is possible to determine the sizes of particles from 1 nm to 5 um. The instrument is also capable of measuring the Zeta potential of particles.

Solid means a substance that is not a liquid or a gas. A solid substance may have one of a variety of forms, including a monolithic solid, a powder, a gel, or a paste.

Phosphatidylcholine (PC) molecules are a subset of the larger set of phospholipids and are commonly used to form liposomes in water. When placed in water without other constituents, the PC forms liposomes. The application of sufficient shear forces to the PC liposomes can reduce the bilayer liposome structures to monolayer structures, including micelles. PC has a head that is water-soluble and a tail that is much less water-soluble in relation to the head. PC is a neutral lipid, but carries an electric dipole moment of about 10 D between the head and the tail, making the molecule itself polar. While "PC" is used throughout this document for convenience, PC may be substituted with or combined with other amphiphilic fats. Preferable amphiphilic fats are isolated from lecithin. As the amphiphilic fat is preferably a phospholipid isolated from lecithin, the named isolates preferably include 80% (w/w) of the specified phospholipid with the remaining constituents being one or more additional phospholipids isolated from the lecithin or other lecithin isolates. Preferred phospholipid lecithin isolates include phosphatidylcholine (PC), phosphatidylethanolamine (PE), phosphatidylinositol (PI), ceramide phosphoryl ethanolamine (Cer-PE), ceramide phosphoryl choline (SPH), and combinations thereof, with PC, PE, and combinations thereof being more preferred. However, all phospholipid lecithin isolates are unexpectedly not interchangeable in forming the nanoemulsion blend as a stable dispersion that is also transparent. In fact, the phosphatidylserine (PS) and phosphatic acid (PA) isolates are not useful when a nanoemulsion blend that is a stable dispersion and is transparent is desired.

Tocopheryl polyethylene glycol succinate 1000 (TPGS) is generally considered a surfactant having a non-polar, oil-soluble "Vitamin E" tail and a polar, water-soluble polyethylene glycol head. While "TPGS" is used throughout this document for convenience, TPGS may be substituted with or combined with other polyethylene glycol surfactants including polysorbate 40, 60, or 80, preferably polysorbate 60 or 80.

Ingestible means capable of being ingested through the mouth by a living mammal while edible means fit to be eaten, thus in contrast to being unpalatable or poisonous. Edible also means that the composition has less than the permitted amount of viable aerobic microorganisms and meets the American Herbal Products Association (AHPA) guidelines for metals, adulterants, toxins, residual solvents, and pesticides.

Endotoxins are present inside a bacterial cell and are released when the cell disintegrates. Endotoxins are sometimes responsible for the characteristic symptoms of a disease. In the context of liver function, endotoxins associated with dysbiosis and gram-negative flora, are reported to irritate the mucosal lining of the gastrointestinal tract and increase inflammation. Such inflammation of the gastrointestinal tract is believed to result in a "leaky" gut that lets bacterial and other toxins slip into the bloodstream from the gastrointestinal tract, thus, triggering a systemic inflammatory response.

Heavy metals include mercury, cadmium, lead, arsenic, nickel, and antimony. For example, mercury is believed to increase inflammation and permeability of the bowel.

Mold toxins include Ochratoxin A; the Aflatoxin group of toxins including B1, B2, G1, and G2; the Trichothecene group of toxins including macrocyclic toxins; and the Gliotoxin derivative toxins. Other mold toxins may be included, but these are the primary toxins for which analytic techniques exist.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

While various aspects of the invention are described, it will be apparent to those of ordinary skill in the art that other embodiments and implementations are possible within the scope of the invention. Accordingly, the invention is not to be restricted except in light of the attached claims and their equivalents.

The invention claimed is:

1. An intra-oral, nanoemulsion blend for enhancing liver performance in animals when orally administered, the blend comprising:
   at least one monolayer surfactant bound particle, where
      the at least one monolayer surfactant bound particle comprises at least one amphiphilic fat, a polyethylene glycol surfactant, an associating oil, and milk thistle;
   at least one bilayer liposome, where
      the at least one bilayer liposome comprises the at least one amphiphilic fat and the polyethylene glycol surfactant forming a capsule, where an interior of the capsule includes water, ethanol, glycerin, and dissolved myrrh; and
   a continuous phase comprising water, ethanol, and glycerin;
   where
      the at least one monolayer surfactant bound particle has a ratio of the amphiphilic fat to the polyethylene glycol surfactant from 1:1.8 to 1:3 by weight,
      the at least one amphiphilic fat is associated with R-Lipoic acid,
      the blend is a stable dispersion that is transparent, and
      the at least one monolayer surfactant bound particle and the at least one bilayer liposome have an average particle diameter from 10 to 100 nanometers as carried by the continuous phase.

2. The blend of claim 1, where the at least one monolayer surfactant bound particle further comprises diindolylmethane, quercetin, and luteolin.

3. The blend of claim 1, where the interior of the capsule further comprises dandelion, gentian, and goldenrod dissolved in the water, ethanol, and glycerin.

4. The blend of claim 1, where the at least one monolayer surfactant bound particle further comprises at least one tocotrienol form of Vitamin E.

5. The blend of claim 1, where the at least one amphiphilic fat is chosen from phospholipid lecithin isolates.

6. The blend of claim 1, where the at least one amphiphilic fat is chosen from phosphatidylcholine (PC), phosphatidylethanolamine (PE), phosphatidylinositol (PI), ceramide phosphoryl ethanolamine (Cer-PE), ceramide phosphoryl choline (SPH), and combinations thereof.

7. The blend of claim 1, where the at least one amphiphilic fat includes at least 30% phosphatidylcholine by weight.

8. The blend of claim 1, where the polyethylene glycol surfactant is chosen from TPGS, polysorbate 80, polysorbate 60, and combinations thereof.

9. The blend of claim 1, where the polyethylene glycol surfactant comprises TPGS.

10. The blend of claim 1, where the associating oil is chosen from medium chain triglycerides (MCT), citrus oil, and combinations thereof.

11. The blend of claim 1, further comprising a micelle.

12. The blend of claim 1, where the milk thistle comprises at least 50% silymarin by weight.

13. The blend of claim 1, where the blend is ingestible and edible.

14. The blend of claim 1, where the at least one monolayer surfactant bound particle and the at least one bilayer liposome have an average diameter from 10 to 60 nanometers.

15. The blend of claim 2, where the ratio of milk thistle to myrrh to R-Lipoic acid is 1:4:4±10% by weight.

16. The blend of claim 1, where the ratio of R-Lipoic acid to diindolylmethane to quercetin is 4:1:0.6±10% by weight.

17. The blend of claim 1 comprising an amphiphilic fat to polyethylene glycol surfactant ratio from 1:1.6 to 1:3 by weight.

18. The blend of claim 1, where the continuous phase constitutes from 70% to 90% by weight of the nanoemulsion blend.

19. The blend of claim 1, where the ratio of glycerin to ethanol in the continuous phase is 1:1±20% by weight.

20. The blend of claim 1, where the ratio of the water to the ethanol and the glycerin in combination is 1:1.5±20% by weight and the ratio of the ethanol to the glycerin is 1:1±20% by weight.

21. The blend of claim 1, where the blend is at least 25% water, 20% glycerin, and 20% ethanol by weight.

22. The blend of claim 2 where at least 60% of a total bloodstream delivered concentration of the milk thistle, the myrrh, and the R-lipoic acid is delivered by transmucosal absorption through the mouth, when 5 mL of the blend is intra-orally administered to a human for a mouth-residency time of 2 minutes.

23. The blend of claim 2 where at least 80% of a total bloodstream delivered concentration of the milk thistle, the myrrh, and the R-lipoic acid is delivered by transmucosal absorption through the mouth, when 5 mL of the blend is intra-orally administered to a human for a mouth-residency time of 2 minutes.

\* \* \* \* \*